United States Patent [19]

Reis et al.

[11] Patent Number: 5,760,872
[45] Date of Patent: Jun. 2, 1998

[54] APPARATUS FOR ALIGNING A FOCUSED BEAM OF LIGHT

[75] Inventors: Werner Reis, Munich, Germany;
Ulrich Klingbeil, Belmont, Mass.;
Andreas Plesch, Sandhausen, Germany

[73] Assignee: G. Rodenstock Instrumente GmbH., Ottobrunn-Riemerling, Germany

[21] Appl. No.: 608,211

[22] Filed: Feb. 28, 1996

Related U.S. Application Data

[63] Continuation of Ser. No. 245,680, May 18, 1994, abandoned.

[30] Foreign Application Priority Data

May 18, 1993 [DE] Germany ............... 43 16 443.9

[51] Int. Cl.⁶ .......................................... A61B 3/10
[52] U.S. Cl. ........................................ 351/205; 359/208
[58] Field of Search ............................... 351/205, 207,
351/208, 211, 212, 213, 214, 220, 221;
359/196, 208

[56] References Cited

U.S. PATENT DOCUMENTS

| | | | |
|---|---|---|---|
| 4,886,351 | 12/1989 | Sabban et al. | 251/221 |
| 4,893,920 | 1/1990 | Webb | 351/205 |
| 5,071,246 | 12/1991 | Blaha et al. | 351/205 |
| 5,177,511 | 1/1993 | Feuerstein et al. | 351/205 |
| 5,198,845 | 3/1993 | Triller | 351/205 |
| 5,268,711 | 12/1993 | Poxleitner et al. | 351/221 |
| 5,396,302 | 3/1995 | Triller et al. | 351/205 |
| 5,430,509 | 7/1995 | Kobayashi | 351/221 |

FOREIGN PATENT DOCUMENTS 0412667  2/1991  European Pat. Off. ............ 351/221

*Primary Examiner*—William L. Sikes
*Assistant Examiner*—James A. Dudek
*Attorney, Agent, or Firm*—Antonelli, Terry, Stout & Kraus, LLP

[57] ABSTRACT

Disclosed is an apparatus for aligning a focused beam of light and, in particular, a laser beam onto a surface using optical elements which image, respectively shape, deflect and align the beam of light.

The present invention is distinguished by a deflecting optical element having, in addition, a focusing effect.

11 Claims, 1 Drawing Sheet

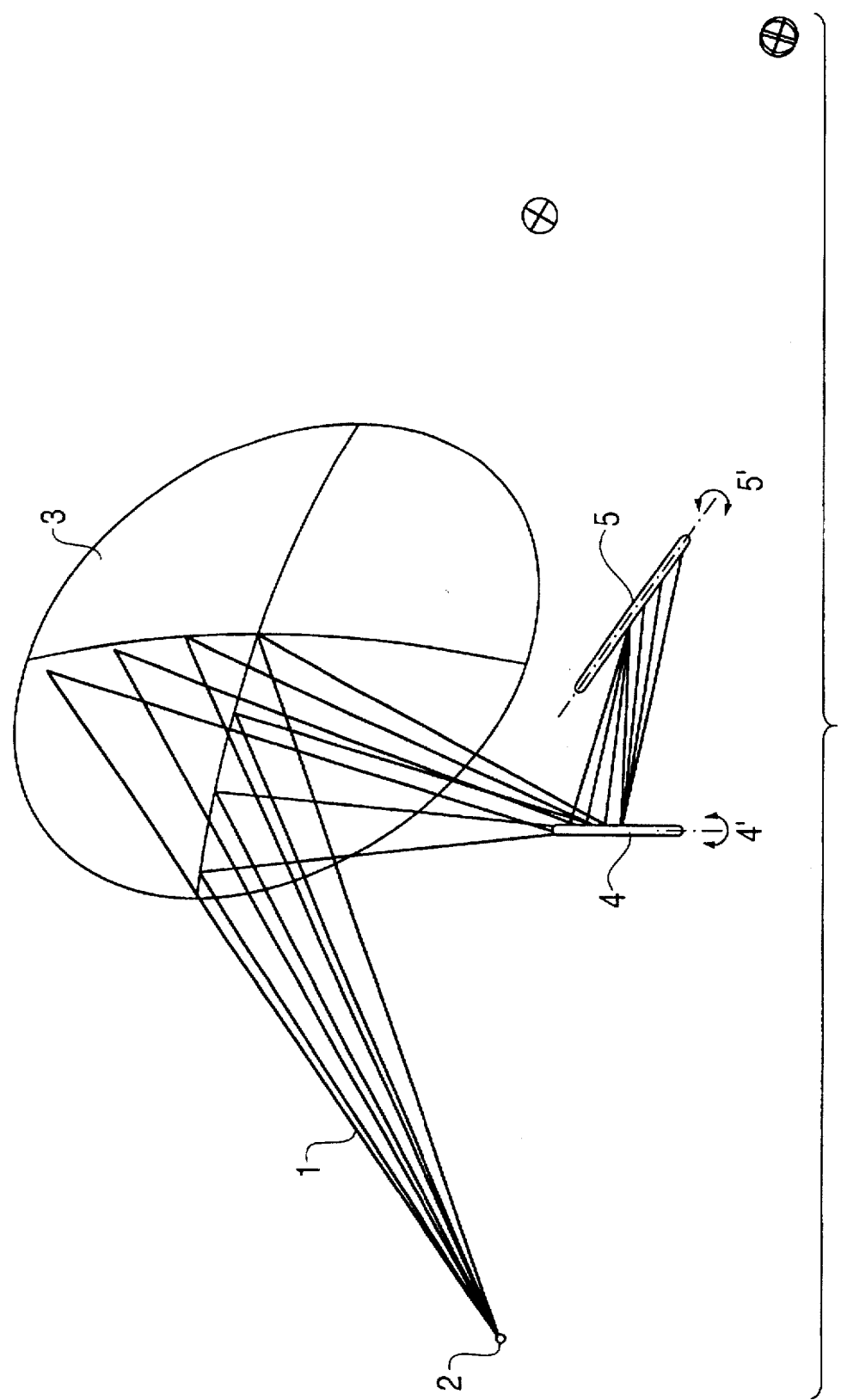

APPARATUS FOR ALIGNING A FOCUSED BEAM OF LIGHT

This application is a continuation of Ser. No. 08/245,680, filed May 18, 1994 now abandoned.

The present invention relates to an apparatus for aligning a focused beam of light and, in particular, a laser beam onto a surface using optical elements which image, respectively shape, deflect and align the light beam.

Apparatus of this type are common knowledge and are required for various purposes, by way of illustration, for marking or labeling work pieces, for processing materials, etc.

However, an especially important area of application of such apparatuses is, also the subsequent, respectively retrofitted, coupling in of the beam, respectively the beams, of one or several treatment lasers in ophthalmological examining instruments, which thereby can also be utilized as treatment, respectively therapeutical instruments.

By way of illustration, mirroring in the beam of a treatment laser, e.g. an Argon ion laser into the beam path of an ophthalmological examining instrument and, in particular, a slit lamp is known from DE-C-33 31 431: for this purpose the beam is led through the arm of the slit-lamp microscope and deflected there by a plane mirror in the direction of the eye so that the laser beam is focused through the main lens of the slit-lamp microscope into the eye to be treated. This manner of guiding the beam has the advantage that the distance between the focusing element and the eye is relatively small so that the laser beam can be focused with a large angle of convergence (i.e. angle of the peripheral rays of the focused pencil of rays). In this way, the energy density reaches high values only the immediate vicinity of the focal "point".

In a number of applications, however, it is desirable if the laser beam is not led coaxially to the examination beam path, but rather, by way of illustration, coaxially to the illumination beam path or in a relatively freely positionable manner to the examination and illumination beam path. In these case, it is frequently necessary to dispose the elements that focus the laser beam at a relatively great distance from the eye to be treated so that the angle of convergence is small due to the thereby required great focal length of the focusing elements and consequently the accompanying drawbacks set in.

Even in coupling in a therapeutical laser beam into a so-called scanning laser ophthalmoscope, like the one described, by way of illustration, in EP-A-O 290 566 and the literature cited therein, no satisfactory solution for coupling in a therapeutical laser beam into the examination beam path has hitherto become known.

EP-A-O 290 566, DE-C-33 31 431 and the literature cited therein are explicitly referred to with regard to the explanation of all the terms not explicitly explained herein.

The object of the present invention is to further improve an apparatus for aligning a focused beam of light, in particular, a laser beam onto a surface using optical elements that image the light beam, respectively shape, deflect and focus it, in such a manner that the distance of the element focusing the light beam from the area is minimized.

A solution to this object in accordance with the present invention is described in claim 1. Further improvements of the present invention are the subject matter of the subclaims.

An element of the present invention is that a deflecting optical element has, in addition, a focusing effect. As the beam path of the processing, respectively treatment, laser usually has to be deflected at least once, by a plane mirror respectively prisms, i.e., optical elements without any focusing effect according to the state of the art, employing a focusing deflecting element and, in particular, a concave mirror (claim 2) does not present any major additional effort.

The deflecting optical element having a focusing effect can be positioned, in particular, immediately in front of the area to be processed so that the laser beam can be focused with a large angle of convergence.

By way of illustration, if the invented apparatus is part of an instrument for examining and treating eyes and, in particular, the fundus oculi having at least one laser, the deflecting optical element having a focusing effect can deflect the light beam (directly) onto the eye (claims 11 and 12), i.e., be positioned in the optical axis of the eye.

It is especially preferable if according to claim 13 the deflecting optical element having a focusing effect is positioned behind the last optical element of the examination instrument in the examination direction immediately in front of the eye to be examined and treated. In this case, it is, furthermore, preferable if the distance between the front surface of the carrier on which the mirror layer is applied and the pupil of the eye is approximately equal to the radius of curvature of the front surface (claim 14).

The apparatus designed in accordance with the present invention can be utilized in combination with various ophthalmological instruments, such as slit lamps, ophthalmoscopes, etc. preferably in scanning laser ophthalmoscopes.

In this event, the deflecting optical element having a focusing effect is preferably positioned in front of the exit window of the "image-forming" scanning laser beam from the examination instrument so that the advantages of the invented apparatus, a larger angle of convergence, etc., especially can be utilized.

Independent of the application of the invented apparatus, it is preferable if the concave mirror is a surface mirror (claim 2). Such a concave mirror deflects the laser beam with little effort and the least imaging errors.

Whenever, in addition, an examination apparatus is employed, it is advantageous if according to claim 4 the surface mirror has a wavelength-selective mirror layer which, in particular, selectively reflects the wavelength of the light source, respectively, of the laser. In this way, the examination beam path is disturbed as little as possible even in the case of an at least almost coaxial guiding of the therapeutical laser beam and examination beam path.

This is also the purpose of the features set forth in claim 5 according to which the carrier of the surface mirror is composed of a material that is transparent for the wavelengths for which the mirror layer is not reflecting. Thus the carrier can, by way of illustration, be made of an optical glass or of a suited plastic material. Insofar as examination occurs through the concave mirror, it is, furthermore, advantageous if the center points of both curved surfaces of the carrier lie at the same point so that the carrier has a constant thickness and, therefore, the beam passing through this carrier neither focuses nor scatters (claim 6).

In any case, however, it is especially advantageous according to claim 7 if the deflecting optical element having a focusing effect, thus by way of illustration the concave mirror, deflects the axis of the beam of light at an angle of 90°. Although in this way an astigmatism is impressed on the beam path, this astigmatism can, however, be advantageous:

In particular, if two mirror elements with no focusing effect, which can be tilted, respectively pivoted, about axes which are not parallel to each other (claim 8), are provided for aligning the light beam, according to claim 9 one mirror element can be placed at the focal point in the sagittal section and the other mirror element at the focal point for the meridional section. This permits, i.a., the pivoting axes of the mirror elements to be perpendicular to each other so that decoupling of the aligning procedure is possible.

The present invention is made more apparent in the single figure of the drawing depicting a preferred embodiment of the present invention.

The invented apparatus for aligning a focused beam of light 1 and, in particular, a laser beam on a surface 2 is provided with a deflecting optical element 3 having a focusing effect. In the depicted embodiment, this element 3 is a concave mirror which is designed as a surface mirror. Especially if the apparatus is part of an eye-examining instrument, the surface mirror can have a wavelength selective mirror layer which, in particular, selectively reflects the wavelength of the light source, respectively of the laser.

Furthermore, two mirror elements 4 and 5 having no focusing effect are provided for aligning the light beam, i.e., two plane mirrors which can be tilted, respectively pivoted about axes 4' and 5', which enclose a 90° angle. A mirror element is positioned at the focal point in the sagittal section and the other mirror element at the focal point for the meridional section.

If the site, by way of illustration, the pupil 1 of the eye is imaged by element 2, two spatially separate sites for the focal points in the sagittal and meridional sections are yielded due to the angle under which element 2 is positioned. The two mirror elements 4 and 5 serving as micromanipulators permit manipulating the light beam in such a manner that all the beams of any deflection intersect at the site of the pupil of the eye.

The present invention for an eye-examination instrument has been described herein without the intention of limiting general applicability.

What is claimed is:

1. An apparatus for aligning a focused beam of light comprising:
   means for providing a beam of light;
   means for focusing the beam of light onto a surface utilizing a plurality of optical elements for imaging, shaping, deflecting and aligning the beam of light, at least one optical element of the plurality of optical elements enabling aligning of the beam of light, and another optical element of the plurality of optical elements enabling deflection and focusing of the beam of light;
   wherein the another optical element enabling deflection and focusing of the beam of light is a concave mirror;
   wherein the concave mirror is a surface mirror;
   wherein the surface mirror includes a wavelength-selective mirror layer for selectively reflecting the wavelength of the light beam; and
   wherein the surface mirror includes a carrier for the surface mirror made of a material which is transparent for wavelengths not reflected by the mirror layer.

2. An apparatus according to claim 1, wherein the beam of light is a laser beam.

3. An apparatus according to claim 1, wherein the carrier has two curved surfaces having center points aligned on a same point so that the carrier has a constant thickness and does not focus or scatter the light beam passing through the carrier.

4. An apparatus according to claim 1, wherein the at least one optical element for enabling alignment of the light beam includes two mirror elements arranged for tilting movement about axes which are not parallel to one another, the two mirror elements having no focusing effect.

5. An apparatus according to claim 11, wherein the apparatus is part of an instrument for examining and treating the fundus oculi of an eye, and the light beam is a laser beam provided by the light beam providing means.

6. An apparatus according to claim 5, wherein the another optical element deflects the laser beam onto the eye.

7. An apparatus according to claim 1, wherein the apparatus is part of an instrument for examining and treating the fundus oculi of an eye, the light beam is a laser beam provided by the light beam providing means, and a distance between a front surface of the carrier and a pupil of the eye is approximately equal to a radius of curvature of the front surface.

8. An apparatus according to claim 7, wherein the instrument is a scanning laser ophthalmoscope.

9. An apparatus for aligning a focused beam of light comprising:
   means for providing a beam of light;
   means for focusing the beam of light onto a surface utilizing a plurality of optical elements for imaging, shaping, deflecting and aligning the beam of light, at least one optical element of the plurality of optical elements enabling aligning of the beam of light, and another optical element of the plurality of optical elements enabling deflection and focusing of the beam of light;
   wherein the at least one optical element for enabling alignment of the light beam includes two mirror elements arranged for tilting movement about axes which are not parallel to one another, the two mirror elements having no focusing effect; and
   wherein one of the two mirror elements is positioned at a focal point in a sagittal section and the other of the two mirror elements is positioned at a focal point for the meridional section.

10. An apparatus according to claim 9, wherein the axes about which the two mirror elements are arranged for tilting movement are pivoting axes which are perpendicular to one another.

11. An apparatus for aligning a focused beam of light comprising:
   means for providing a beam of light;
   means for focusing the beam of light onto a surface utilizing a plurality of optical elements for imaging, shaping, deflecting and aligning the beam of light, at least one optical element of the plurality of optical elements enabling aligning of the beam of light, and another optical element of the plurality of optical elements enabling deflection and focusing of the beam of light;
   wherein the beam of light is a laser beam;
   wherein the apparatus is part of an instrument for examining and treating the fundus oculi of an eye, and the light beam is a laser beam provided by the light beam providing means;
   wherein the another optical element deflects the laser beam onto the eye; and
   wherein the another optical element is positioned behind the last optical element of an eye-examination beam path in an examination direction immediately in front of the eye to be examined and treated.

* * * * *